United States Patent
Buss et al.

[11] Patent Number: 6,000,940
[45] Date of Patent: Dec. 14, 1999

[54] SURGICAL BUR SHANK AND LOCKING COLLET MECHANISM

[76] Inventors: Rick A. Buss; Shaher Ahmad, both of 3750 Realty Rd., Dallas, Tex. 95244; Michael F. Wei, 177 N. El Camino Real, San Mateo, Calif. 94401

[21] Appl. No.: 09/069,342

[22] Filed: Apr. 29, 1998

Related U.S. Application Data

[60] Provisional application No. 60/045,246, May 1, 1997, provisional application No. 60/045,249, May 1, 1997, and provisional application No. 60/045,250, May 1, 1997.

[51] Int. Cl.$^6$ ..................................................... A61C 1/14
[52] U.S. Cl. ............................................................ 433/127
[58] Field of Search .............................. 606/167; 433/128, 433/129, 127

[56] References Cited

U.S. PATENT DOCUMENTS

| | | | |
|---|---|---|---|
| 3,631,597 | 1/1972 | Lieb | 32/26 |
| 3,775,851 | 12/1973 | Flatland | 32/26 |
| 5,490,683 | 2/1996 | Mickel et al. | 279/75 |
| 5,584,689 | 12/1996 | Loge | 433/128 |

Primary Examiner—Michael Buiz
Attorney, Agent, or Firm—John E. Wagner

[57] ABSTRACT

A collet for holding a rotatable tool such as a bur or drill bit having a stepped shaft including a drive shaft having a stepped internal diameter mating with the external diameter of the bur or drill shaft, a plurality of hardened balls mounted in openings in the sleeve, a locking sleeve having a tapered surface movable with the force of a spring against the balls to force the balls against the shaft to lock the shaft in the sleeve. A rotatable locking collar is movable to release the spring force to release the shaft for removal and replacement of the tool.

20 Claims, 1 Drawing Sheet

SURGICAL BUR SHANK AND LOCKING COLLET MECHANISM

This application claims the benefit if U.S. Provisional Patent Applications:

60/045,246 Filed May 1, 1997, now U.S. patent application, Ser. No. 09/069,474, filed Apr. 29, 1998 for BLADE CAPTURE HUB FOR SAGITTAL OR OSCILLATING SAW AND BLADES THEREFOR;

60/045,249 Filed May 1, 1997, now U.S. patent application, Ser. No. 09/069,349, filed Apr. 29, 1998 ELECTRONIC CONTROLLED SURGICAL POWER TOOL; and 60/045,250, Filed May 1, 1997 now this present U.S. patent application Ser. No. 09/069,342, filed Apr. 29, 1998 for SURGICAL BUR SHANK AND LOCKING COLLET.

BRIEF DESCRIPTION OF THE INVENTION

Applicants have provided a shank and collet structure which is believed to constitute a significant improvement over similar devices now in use for securing tools such as burs or drill bits in a high speed surgical drilling device. Such tools may operate at speeds up to 70,000 rpm making it essential that the bur or drill bit shaft be secured in an absolutely concentric position in the drill drive shaft and also that it is secured axially. Since the use of such drilling devices usually take place in an operating room, it is desirable that the bur or drill bit shafts be easily, quickly and conveniently removed and replaced. It is also necessary that such bur or drill shafts be firmly secured in the drill drive shaft such that, under high speeds, they do not whip or become dislodged or break apart.

The bur shank and collet mechanism of the present invention meets the above requirements through the use of precisely manufactured bur or drill shafts placed in a drill drive shaft with a locking mechanism assuring concentric shaft retention. A three-ball retention mechanism holds the bur or drill shaft securely in position through a wedging action which forces the balls against and slightly into the bur or shaft. A convenient locking collar enables a surgeon to, by turning the locking collar, unlock the ball retention mechanism to free one bur or drill shaft and insert another. A turn of the locking collar in the opposite direction causes the aforementioned wedging action to take place, forcing the balls against the newly installed bur or drill shaft.

BRIEF DESCRIPTION OF THE DRAWING

This invention may be more clearly understood with the following detailed description and by reference to the drawing in which.

DETAILED DESCRIPTION OF THE INVENTION

Figure 1:
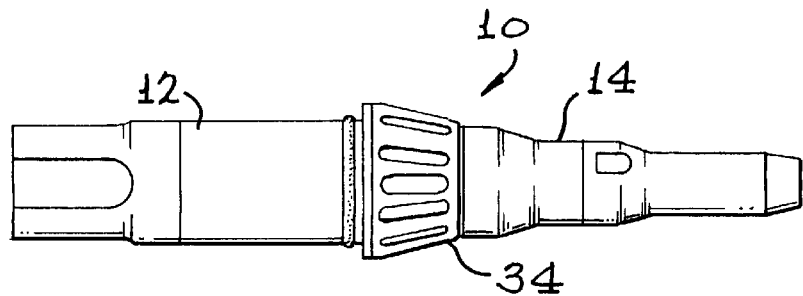
FIG. 1 is a side elevational view of a bar shank and lock for use on surgical drill systems.

Referring to the drawing, a drill 10 designed to be driven by an electric motor (unshown) includes a locking collet mechanism 11 having, inter alia, a housing 12 and a bur guard 14 which enclose an internally stepped drive shaft 18 designed to receive and hold matching bur or drill shaft 28. The bur guard 14 encloses a ball bearing assembly 16 having its inner race secured to a drive shaft 18 driven by a drill motor not part of the present invention. A retention structure includes three balls 20 (only one of which is shown) captured each in one of three openings 120° apart in drive shaft 18. The three-ball retention structure also includes a locking sleeve 22 over drive shaft 18 with a tapered inside surface 24 in contact with three balls 20. A locking spring 26 urges locking sleeve 22 to the right, forcing balls 20 tightly against a bur or drill shaft 28 to secure shaft 28 in drive shaft 18. The hardness of balls 20 is substantially greater than the hardness of shaft 28 so that balls 20 actually deform the metal of shaft 28 slightly when shaft 28 is locked in position. This deformation engagement between balls 20 and the reduced diameter portion 29 of the bur or drill shaft 28 provides positive locking of the bur shaft.

Housing 12 also includes a helical or S-shaped groove 30 in which are positioned a pair of balls 32 in contact with a locking collar 34. Balls 32 also are seated in a radial groove in a locking ring 36 which is urged to the left by a spring 38.

Figure 2:
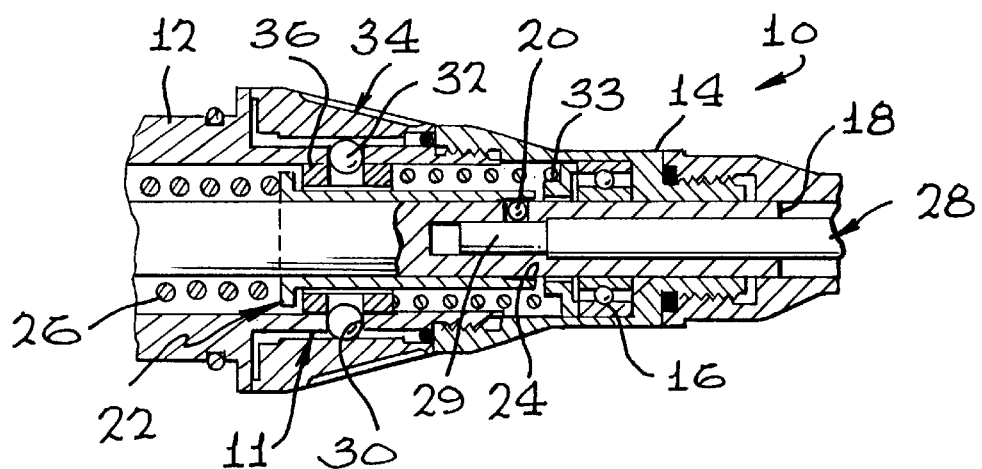
FIG. 2 is a sectional view through our surgical bur or drill bit shank and locking collet mechanism.

With the parts in the position illustrated in FIG. 2, the bur or drill shaft 28 is securely locked in position by balls 20. Balls 32 are in their maximum right hand position, as illustrated, because the locking collar 34 has been turned to force locking ring 36 and balls 32 to the right. When locking collar 34 is turned in the opposite position, balls 32 are permitted to travel in helical or S-shaped groove 30 to the left under the force of spring 38 acting through collar 34 and the walls of helical or S-shaped groove 30. This permits locking ring 36 to force locking sleeve 22 to the left releasing balls 20 from the surface of bur or drill shaft 28 and permitting shaft 28 and bur to be withdrawn.

Figure 3:
FIG. 3 is a side elevational view of an improved bur intended for use with the bur shank and locking detail of this invention.

For this particular surgical application standard burs have a diameter of 0.0924/0.0919". At a point behind (proximal to) the front ball bearing assembly 16, the diameter of the drive shaft 18 is reduced so that to fit this drive shaft, the proximal end 29 of the bur shaft 28 is reduced to 0.081/0.079". This reduction in diameter is shown in FIG. 3. The main body of the bur shaft is of full diameter so that the full diameter of the bur shaft is not compromised in strength to absorb side or bending loading during use. The stepped down diameter of the drive shaft 18 at the location of the locking balls allows a reduced overall drill housing diameter toward the working (distal) end to allow maximum visibility to the surgeon of the working end of the bur or drill. The neck down feature is apparent in FIG. 1.

When a spent bur or drill is withdrawn, as described above, a new bur or drill of the type shown in FIG. 3 can then readily be inserted in drive shaft 18, after which locking collar 34 is then turned in the opposite direction forcing balls 32 to the right and carrying locking ring 36 to the right, compressing spring 38 and causing locking sleeve 22 to slide to the right under the force of spring 26. This causes tapered inside surface 24 to force balls 20 tightly against the proximal end 29 of the new bur or drill shaft 28 in the same positive locking engagement as for the previous bur.

The above-described embodiments of the present invention are merely descriptive of its principles and are not to be considered limiting. The scope of the present invention instead shall be determined from the scope of the following claims including their equivalents.

We claim:

1. A collet assembly for securely holding a rotatable tool having a cylindrical shaft with a reduced diameter at its proximal end comprising:

a drive shaft including a cylindrical recess in a wall of the distal end thereof for receiving tool shaft, the internal diameter of the cylindrical recess in said drive shaft being reduced at its proximal end over a portion of the length of said drive shaft, said drive shaft having a plurality of openings in the portion of the drive shaft defining said cylindrical recess;

a plurality of hardened balls positioned in said openings;

said balls being slightly larger than the wall thickness of said drive shaft;

said openings in said drive shaft wall being located in the reduced internal diameter portion of said drive shaft cylindrical recess;

means rotatably driving said drive shaft;

locking means securing said tool shaft in said drive shaft, said locking means comprising a locking sleeve coaxially outward of said drive shaft having an internal tapered surface and a flange;

resilient means urging said locking sleeve toward said hardened balls to force said balls against the reduced diameter distal end of said tool shaft; and operator-operated means for releasing said locking means to permit insertion and removal of said tool.

2. A collet as claimed in claim 1 wherein said collet includes a housing, a bearing in said housing supporting said drive shaft, and the reduced diameter part of said drive shaft is proximal of said bearing.

3. A collet assembly for securely holding a rotatable tool having a shaft with a reduced diameter at its proximal end comprising:

a drive shaft including a cylindrical recess in its distal end for receiving said tool shaft;

means rotatably driving said drive shaft;

a housing enclosing said drive shaft;

a locking sleeve coaxially outward of said drive shaft;

securing means operatively connected to said locking sleeve for securing a tool shaft in said drive shaft;

the internal diameter of said drive shaft recess over a portion of its length at the proximal end of said sleeve being significantly less than its diameter at its distal end;

said securing means being located in the reduced diameter portion of said drive shaft recess;

resilient means urging said sleeve in a direction to cause said securing means to secure said tool shaft in said drive shaft in the region of said significantly less diameter of said drive shaft recess;

a rotatable locking collar; and means interposed between said locking collar and said locking sleeve for moving said securing means to a securing position when said locking collar is rotated in a first direction and for moving said securing means in a releasing direction when said locking collar is rotated in a second direction;

whereby said collet assembly will not lock a tool shaft which does not include a reduced diameter proximal end.

4. A collet as claimed in claim 3 wherein said housing includes a bearing supporting said drive shaft and the reduced diameter part of said drive shaft is proximal of said bearing.

5. A collet as claimed in claim 3 wherein over a portion of its length at the proximal end of said sleeve, the internal diameter of said drive shaft is significantly less then its diameter at its distal end and the diameter of said tool shaft at its proximal end is correspondingly less than its diameter at its distal end.

6. A collet as claimed in claim 3 wherein said drive shaft has a plurality of openings, said securing means comprises a plurality of hardened balls positioned in said openings, said balls being slightly larger in diameter than the wall thickness of said drive shaft;

said locking sleeve having an internal tapered surface and a flange; and said resilient means urging said locking sleeve in a direction to force said balls against said tool shaft in the significantly less diameter portion of said drive shaft.

7. A collet as claimed in claim 6 wherein said hardened balls are located in the reduced internal diameter portion of said drive shaft.

8. A collet for securely holding a rotatable tool having a shaft comprising:

a drive shaft for receiving said tool shaft having a plurality of spaced openings;

a plurality of hardened balls in said openings, said balls being slightly larger in diameter than the wall thickness of said drive shaft;

means rotatably driving said drive shaft;

a housing enclosing said drive shaft;

a locking sleeve coaxially outward of said drive shaft having an internal tapered surface;

a first spring urging said locking sleeve toward said hardened balls such that said tapered surface forces said balls against said tool shaft;

a second spring urging said locking sleeve in the opposite direction from the force of said first spring;

a rotatable locking collar coaxially outward of said locking sleeve; and means interposed between said locking collar and said locking sleeve for translating said locking sleeve against said hardened balls when said locking collar is rotated in a first direction and for translating said locking sleeve away from said hardened balls when said locking collar is rotated in the opposite direction.

9. A collet as claimed in claim 8 wherein said housing includes a bearing near its distal end whose inner race is secured to said drive shaft.

10. A collet as claimed in claim 8 wherein the internal diameter of said drive shaft is significantly reduced from a point proximal of said bearing to its proximal end.

11. A collet as claimed in claim 8 wherein said drive shaft has a reduced internal diameter at its proximal end and said tool shaft has a complementary stepped surface.

12. A collet as claimed in claim 8 wherein over a portion of its length at the proximal end of said drive shaft, the internal diameter of said drive shaft is significantly less then its diameter at its distal end and the diameter of said tool shaft at its proximal end is correspondingly less than its diameter at its distal end.

13. A collet for securely holding a rotatable tool having a shaft, said shaft having a reduced diameter at its proximal end comprising:

a drive shaft for receiving said tool shaft, said drive shaft having a reduced diameter at its proximal end and having a plurality of spaced openings;

a plurality of hardened balls carried in said openings, said balls being slightly larger in diameter than the wall thickness of said drive shaft;

a housing enclosing said drive shaft and a bearing in said housing at the distal end thereof;

means rotatably driving said drive shaft to turn said shaft;

a locking sleeve coaxially outward of said drive shaft having an internal tapered surface and an external flange;

a first spring urging said locking sleeve toward said hardened balls such that said tapered surface forces said balls against the proximal end of said tool shaft;

a helical groove in said housing;

a plurality of balls in said helical groove;

a locking collar coaxially outward of said balls;

a locking ring in contact with said balls and a second spring urging said locking ring toward said external flange;

whereby rotation of said locking collar in one direction causes said balls to be moved axially in said groove and permitting said first spring to force said tapered surface against said hardened balls and said hardened balls against said tool shaft to firmly secure said tool shaft in said drive shaft and rotation of said locking collar in the opposite direction causes said balls to be moved in the opposite direction under the force of said second spring to force the tapered surface away from said hardened balls and releasing said tool shaft.

14. For use with a collet including a housing, a drive shaft with a plurality of openings near its proximal end, a plurality of balls in said openings, said balls being slightly larger in diameter than the wall thickness of said drive shaft and a bearing in said housing supporting said drive shaft, said drive shaft having an internal axial opening whose diameter is smaller at its proximal end than at its distal end;

a rotatable surgical tool for performing a surgical procedure comprising a shaft having a smaller diameter proximal end proximal of said bearing and secured by clamping said balls against said proximal end; a larger diameter intermediate shaft portion; and a rotatable surgical instrument at the distal end thereof.

15. A surgical tool as claimed in claim 14 wherein said larger diameter intermediate shaft portion mates with the distal end of said drive shaft.

16. A surgical tool for use with a source of rotation including a drive shaft with a recess therein of two different diameters comprising:

a shaft having a proximal end, a distal end, and an intermediate shaft portion having a predetermined diameter;

said distal end having a surgical head for providing a surgical procedure upon rotation of said shaft;

said proximal end being of different diameter from said intermediate shaft portion;

said proximal end having a predetermined length to correspond to the depth of the lesser of the two diameters of a mating drive shaft;

whereby the securing of said tool for rotatable operation employs the securing of said different diameter proximal end within said drive shaft recess shaft portion.

17. A surgical tool in accordance with claim 16 wherein at least a portion of said intermediate shaft portion mates with a source of rotation and said proximal end is adapted for clamping engagement with the same source of rotation.

18. A surgical tool in accordance with claim 16 wherein said proximal end is of smaller diameter than said intermediate shaft portion.

19. A collet for securely holding a rotatable tool having a shaft with a reduced diameter at its proximal end comprising:

a drive shaft for receiving said tool shaft, the internal diameter of said drive shaft being reduced at its proximal end over a portion of its length;

means rotatably driving said drive shaft;

a housing enclosing said drive shaft;

means securing said tool shaft in said drive shaft including resilient means;

a rotatable locking collar; and means interposed between said locking collar and said securing means for moving said securing means to a securing position when said locking collar is rotated in a first direction and for moving said securing means in a releasing direction when said locking collar is rotated in a second direction;

wherein said drive shaft has a plurality of openings, a plurality of hardened balls are positioned in said openings, said balls being slightly larger in diameter than the wall thickness of said drive shaft;

said securing means comprises a locking sleeve coaxially outward of said drive shaft having an internal tapered surface and a flange, and said resilient means urges said locking sleeve in a direction to force said balls against said shaft; and wherein a second resilient means urges said locking sleeve in the opposite direction from said first resilient means when said locking collar is rotated in said second direction.

20. A collet for securely holding a rotatable tool having a shaft with a reduced diameter at its proximal end comprising:

a drive shaft for receiving said tool shaft, the internal diameter of said drive shaft being reduced at its proximal end over a portion of its length;

means rotatably driving said drive shaft;

a housing enclosing said drive shaft;

means securing said tool shaft in said drive shaft including resilient means;

a rotatable locking collar; and means interposed between said locking collar and said securing means for moving said securing means to a securing position when said locking collar is rotated in a first direction and for moving said securing means in a releasing direction when said locking collar is rotated in a second direction;

wherein said drive shaft has a plurality of openings, a plurality of hardened balls are positioned in said openings, said balls being slightly larger in diameter than the wall thickness of said drive shaft;

said securing means comprises a locking sleeve coaxially outward of said drive shaft having an internal tapered surface and a flange, and said resilient means urges said locking sleeve in a direction to force said balls against said shaft; and wherein said means interposed between said locking collar and said locking sleeve comprises a helical groove in said housing, a plurality of balls in said helical groove, a locking ring in contact with said balls and a second resilient member urging said locking ring toward said flange.

\* \* \* \* \*